(12) United States Patent
Bennink et al.

(10) Patent No.: US 6,506,390 B2
(45) Date of Patent: Jan. 14, 2003

(54) PROGESTOGEN-ANTI-PROGESTOGEN REGIMENS

(75) Inventors: Herman Jan Tijmen Coelingh Bennink, Driebergen (NL); Pieter M. Verbost, Heesch (NL)

(73) Assignee: Akzo Nobel, Annheim (NL)

( * ) Notice: Subject to any disclaimer, the term of this patent is extended or adjusted under 35 U.S.C. 154(b) by 0 days.

(21) Appl. No.: 09/757,048

(22) Filed: Jan. 8, 2001

(65) Prior Publication Data

US 2001/0027189 A1 Oct. 4, 2001

Related U.S. Application Data

(63) Continuation of application No. 09/194,134, filed as application No. PCT/EP97/03288 on Jun. 23, 1997, now abandoned.

(30) Foreign Application Priority Data

Jun. 25, 1996 (EP) ............................................. 96201744

(51) Int. Cl.$^7$ ................................................. A61K 9/00
(52) U.S. Cl. ...................... 424/400; 424/423; 424/464; 424/465; 424/451; 424/456; 514/169; 514/170
(58) Field of Search ................................. 424/423, 464, 424/465, 451, 456, 400; 514/169, 170

(56) References Cited

U.S. PATENT DOCUMENTS

| 5,521,166 A | 5/1996 | Grubb | 514/170 |
| 5,827,843 A | 10/1998 | Koninckx | 574/170 |

FOREIGN PATENT DOCUMENTS

| DE | 43 44 463 | 3/1995 |
| WO | WO 93 21927 | 11/1993 |
| WO | WO 94 04156 | 3/1994 |
| WO | WO 96 15794 | 5/1996 |

OTHER PUBLICATIONS

Kekkomen et al., Fertility and Sterility 1990, vol. 53, p. 747–750.

Kekkomen et al., Fertility and Sterility 1993, vol. 60, p. 610–615.

The Physicians' Desk Reference, 52$^{nd}$ Edition, p. 306, 326–327 (Medical Economics Company 1998).

Ghosh et al., "Luteal phase contraception with mifepristone (RU486) in the rhesus monkey" Indian J. Physiol Pharmacol. vol. 1 p. 17–22 (Jan. 1994).

Katkam et al., "Onapristone (ZK 98.299): a potential anti-progestin for endometrial contraception" Am J. Obstet Gynecol. vol. 173 p. 779–787 (Sep. 1995).

*Primary Examiner*—Thurman K. Page
*Assistant Examiner*—Lakshmi Channavajjala
(74) *Attorney, Agent, or Firm*—Mark W. Milstead; William M. Blackstone

(57) ABSTRACT

A contraceptive and/or HRT (hormone replacement therapy) kit comprising sequential daily dosage units each containing as the sole contraceptively effective ingredient a progestogen, or as the effective ingredient for HRT a progestogen with or without an estrogen or an estrogen only, and further two or more dosage units comprising an anti-progestogen. The present invention also provides contraceptive and HRT methods comprising administering daily dosage units of a progestogen and anti-progestogen.

18 Claims, No Drawings

PROGESTOGEN-ANTI-PROGESTOGEN REGIMENS

This application is a continuation of U.S. Ser. No. 09/194,134, filed Nov. 20, 1998, now abandoned, which is the U.S. National Phase of PCT/EP97/03288, filed Jun. 23, 1997.

FIELD OF THE INVENTION

The invention relates generally to progestogen-anti-progestogen regimens for use in contraception and hormone replacement therapy, and more specifically for contraception to progestogen-anti-progestogen regimens involving only the administration of a progestogen and an anti-progestogen.

BACKGROUND OF THE INVENTION

It has been known for some time that contraception can be achieved by the oral administration of sufficient quantities of a progestogen to a female of child-bearing age. Contraceptive preparations that minimize the incidence of menstrual spotting, break through bleeding, variations in menstrual cycle length and amenorrhea are preferred. It is further preferred to use contraceptive regimens that minimize the amounts of estrogens and progestogens used. Preparations that fulfill many of these requirements are disclosed in WO 93/21927, wherein a contraceptive regimen free from estrogens is described, the active ingredient being a progestational agent and intermittently an anti-progestogen. The regimen used is a regimen wherein only levonorgestel is administered as the progestogen, except that on days 1, 30, 60, 90, 120, 150, and 180 a dosage of the anti-progestogen RU 486 is administered. In fact the regimen is a progestogen-only regimen, interrupted by anti-progestogen administration at the beginning of each cycle. Although this regimen is a considerable improvement over existing regimens comprising estrogens, the bleeding profile is still not perfect since it recurs slowly after an almost bleeding-free interval, and further improvement is therefor desirable.

"Progestogen-only pills" are a preferred method of contraception for breast-feeding mothers, older women, women for whom estrogen is contraindicated, women who are hypertensive, and women who develop migraine headaches when taking a combined pill (i.e. one containing an estrogen and progestogen component). See, e.g. "Contraception for women over the age of 35", *IPPF Medical Bulletin*, 22: 3–4 (1988) and P. W. Howie "The progestogen-only pill", *Brit. J. Obstet. Gynaecol.*, 92: 1001–2 (1985). While different progestogen-only regimens have been described, they are still associated with incomplete ovulation inhibition, and relatively high failure rates. Vessey et al "Progestogen-only oral contraception. Findings in a large prospective study with special reference to effectiveness", *Brit. J. Family Planning*, 292: 526–30 (1986). It has been suggested to increase the daily dosage of progestogen in order to induce complete ovulation inhibition, however such an increase in dosage also increases the frequency of intermenstrual bleeding (i.e. "spotting"), which is clearly not desired. E. Diczfalusy et al, *Progestogens in Therapy*, p. 150 (Raven Press, NY 1983).

Moreover, a high prevalence of functional ovarian cysts have been reported with progestogen-only contraceptive regimens, which resolve after discontinuation of the progestogen-only contraceptive. Fotherby, K. "The Progestogen-pill", in: Filshie et al eds. *Contraception: Science and Practice*, pp. 94–108 (1989), and Howie, supra. A need exists for a progestogen-only contraceptive regimen which more effectively inhibits ovulation, while still not increasing the frequency of intermenstrual bleeding, or leading to persistent functional ovarian cysts. The solution to this need by adding intermittently an anti-progestogen needs further elaboration.

SUMMARY OF THE INVENTION

Surprisingly, it has now been found that apart from administering an anti-progestagen at the beginning of a cycle, by selecting one or more additional days during the cycle, preferably one day in the middle of the cycle, on which the anti-progestogen is administered, whereas over the rest of an entire menstrual cycle (e.g. 28 days) desogestrel or 3-ketodesogestrel is administered as the progestogen at certain specified dosages, complete ovulation inhibition is achieved, while retaining good cycle control and almost completely decreasing the amount of spotting.

The invention thus includes a drug delivery system for contraceptive use containing daily oral dosage units, each unit containing a progestogen, and two or more units comprising an anti-progestogen, one of which is administered at the end and the others orderly divided through the cycle (if one: in the middle of the cycle).

The invention also includes a drug delivery system for HRT (hormone replacement therapy) containing daily oral dosage units, each unit comprising a progestogen with or without an estrogen or an estrogen only, and two or more dosage units comprising an anti-progestogen, one of which is preferably administered at the beginning and the others orderly divided through the cycle (if one: in the middle of the cycle).

In general terms the invention relates to a contraceptive and/or HRT (hormone replacement therapy) kit comprising sequential daily dosage units for oral administration each comprising as the sole contraceptively effective ingredient a progestogen, or as effective ingredient for HRT a progestogen with or without an estrogen or an estrogen alone, and further two or more units comprising an anti-progestogen.

If desired the kits may contain placebo pills to bridge two periods of administration of active ingredients. This is usual for contraceptive regimens containing less than 28 dosage units, in order to obtain a kit still having 28 pills (the usual cycle).

The invention also includes a pharmaceutical product (i.e. the dosage units or the package containing the dosage units), a method of using the product, and a process of manufacturing the pharmaceutical product.

The invention also includes a method of providing contraception and/or HRT for a pre-, peri-, or post-menopausal woman involving administering to the woman the above-mentioned regimens.

DETAILED DESCRIPTION OF THE INVENTION

Progestogens for use with the invention are 3-ketodesogestrel (etonogestrel), desogestrel, gestodene, levonorgestel, norgestrel and other progestogens commonly used for contraception and HRT. Desogestrel has the chemical name 13-ethyl-11-methylene-18,19-di-nor-17α-pregn-4-en-20-yn-17-ol, and is the preferred progestogen. Desogestrel is believed to be metabolized in the body into 3-ketodesogestrel. Preferably the dosage units contain 75 µg of desogestrel or 3-ketodesogestrel, or an amount of other progestogens having the equivalent effect as 75 µg of desogestrel. Based on practically applied doses, levonorgestrel, desogestrel, and 3-keto-desogestrel are relatively equipotent in progestogenic activity. Gestodene is approximately 1.5 times as potent as these compounds. Norgestrel is about one-half as potent as levonorgestrel.

The anti-progestogen can be an inhibitor of progesterone synthesis, such as epostane, azastene or trilostane (Creange, Contraception 24, 289, 1981; Drugs of the Future 7, 661, 1982, van der Spuy et al., Contraception 35, 111, 1987; U.S. Pat. No. 3,296,255) or a progesterone receptor antagonist, or any such pharmaceutically suitable agent that counteracts the normal biological activity of progesterone, such as antibodies or ligands bindable to progestogens or to the progesterone receptor.

A suitable anti-progestogen is a progesterone receptor antagonist. For example RU486, Onapristone, Org 31710 [(6α,11β,17β)-11-(4-dimethylaminophenyl)-6-methyl-4', 5'-dihydrospiro[estra-4.9-diene-17,2'-(3'H)-furan]-3-one], and Org 33628 [11β,17α)-11-(4-acetylphenyl)-17,23-epoxy-19,24-dinorchola-4,9,20-trien-3-one] are particularly suitable in the practice of the present invention.

Suitable amounts of anti-progestogen are for example 0.1 to 300 mg, and preferably 0.5 to 150 mg of Org 31710 or such amounts of other anti-progestogens which have equivalent activity. The anti-progestogen is administered at the beginning of the cycle, preferably on day 1, and in the middle of the cycle, preferably day 14. More generally, the first of the anti-progestogen dosage units may be administered between days 1 and 3 (the beginning of the cycle), and the second between days 12 and 16 (the middle of the cycle). In the case of more than one additional day of anti-progestagen administration, these additional days may be, e.g., in the middle of the remaining phases, i.e. anti-progestagen then is administered once a week. Maximally, the anti-progestagen can be administered every 4 days, i.e. for a cyclus of 28 days the number of dosage units comprising anti-progestagen is two to seven. Every 5–7 days is preferred, but it is most preferred that anti-progestagen be administered only one time additionally, i.e. in total twice a month. Particularly in the embodiments in which anti-progestagen is administered more than one time additionally, it is preferred to administer it simultaneously with progestagen, i.e. the anti-progestagen does not substitute the progestagen but comes in addition. It is important that the anti-progestagen is administered only one day in a row. For HRT regimens it is desired for the anti-progestogen to be dosed in as low an amount as is capable of inhibiting bleeding, without inducing menses.

In the method of this invention the contraceptive and/or HRT kit consists of four phases, in which the first phase is a single dosage unit comprising an anti-progestogen and optionally a progestogen, the second phase containing progestogen, estrogen or a mixture thereof, the third phase comprising an anti-progestogen and optionally a progestogen, and the fourth phase containing progestogen, estrogen or a mixture thereof.

Preferably the dosage of the anti-progestogen in the third and optional further phases is lower than the dosage of the anti-progestogen in the first phase. More preferably the first phase consists of 10 to 150 mg of Org 31710, and most preferably 25 mg of Org 31710, and the third phase (and any optional subsequent phase) consists of 0.5 to 25 mg, more preferably of 2.5 to 12.5 mg, and even more preferably of 5 mg of Org 31710. In the case of a more than four-phase regimen involving more than two times administration of anti-progestagen, the first phase dosage will generally be the same as above, but it is possible to further decrease the dosage in the subsequent phases.

For HRT regimens dosage units comprising the anti-progestogen units as above and units comprising an estrogen, progestogen or mixtures thereof are envisaged. Estrogens which can be used include 17β-estradiol and ethinyl estradiol. Mestranol (17-α-ethinyl estradiol 3-methylether) and conjugated estrogens are also useful estrogens. Suitable amounts of ethinyl estradiol per dosage unit are between 0.005 and 0.1 mg. Of course amounts having equivalent activity of other estrogens can also be used. As an approximation, 1 mg of 17β-estradiol is equivalent in estrogenic activity to 0.015 mg of ethinyl estradiol and 0.030 mg of mestranol.

The progestogen and anti-progestogen are incorporated into dosage units for oral administration. The term "dosage unit" generally refers to physically discrete units suitable as unitary dosages for humans, each containing a predetermined quantity of active material calculated to produce the desired effect, for instance tablets, pills, powders, suppositories, capsules and the like.

Methods and compositions for making such dosage units are well-known to those skilled in the art. For example, conventional techniques for making tablets and pills, containing active ingredients, are described in the standard reference, Gennaro et al., Remington's Pharmaceutical Sciences, (18th ed., Mack Publishing Company, 1990, see especially Part 8: Pharmaceutical Preparations and Their Manufacture).

For making dosage units, e.g. tablets, the use of conventional additives, e.g. fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Lactose is a preferred carrier. Mixtures of carriers can also be used.

A process of manufacturing the kit of the invention comprises mixing predetermined quantities of progestogen (for instance desogestrel, 3-ketodesogestrel, or mixtures thereof) or anti-progestogen (for instance Org 31710) with predetermined quantities of excipients and converting the mixture into dosage units containing progestogen or anti-progestogen.

For HRT regimens unit dosages may be obtained by mixing predetermined quantities of progestogen and estrogen.

Preferred kits contain a total of 20 to 32 of said daily sequential dosage units.

Converting the mixture into dosage units generally involves molding the mixture into a tablet, filling a capsule with a dried mixture, or filling a capsule with a wet mixture. A preferred process of manufacturing the pharmaceutical product according to the invention involves incorporating the desired dosages of contraceptive steroid (for example desogestrel, 3-ketodesogestrel, or mixtures thereof) into tablets by techniques such as wet granulation tableting techniques. The package containing the dosage units will contain between 7 and 180, preferably 28, dosage units.

While the description hereinbefore refers to daily dosage units making up the anticonceptive or HRT kit, the method of treatment according to the invention extends to any other suitable form of administration. Therefore, the invention relates to pharmaceutical preparations capable of releasing progestagen and anti-progestagen, optionally simultaneously, in accordance with the regimen described above. Thus the administration in four or more phases of anti-progestagen and progestagen can be effectuated not only through tablets, but also by means of an implant system, a vaginal ring, injectable systems, transdermal systems, or by any combination thereof (particularly: the progestagen administered as a tablet, the anti-progestagen in the form of a non-oral system such as an implant).

The invention is further explained by the following illustrative examples.

EXAMPLE I

The following coated tablets intended for once daily administration were made: Composition (per tablet):

TABLET I

| Compound | Amount (mg/tablet) |
| --- | --- |
| desogestrel | 0.075 |
| corn starch | 6.500 |
| povidone | 1.950 |
| stearic acid | 0.650 |
| colloidal silicone dioxide | 0.650 |
| dl-α-tocopherol | 0.080 |
| lactose | qsad 65.000 |
| Coating layer: (filmcoat-dry) | |
| hydroxypropylmethylcellulose | 0.75 |
| polyethylene glycol 400 | 0.15 |
| titanium dioxide | 0.1125 |
| talc | 0.1875 |

TABLET II

| Compound | Amount (mg/tablet) |
| --- | --- |
| Org 31710 | 25 |
| corn starch | 6.500 |
| povidone | 1.950 |
| stearic acid | 0.650 |
| colloidal silicone dioxide | 0.650 |
| dl-tocopherol | 0.080 |
| lactose | qsad 65.000 |

TABLE III

| Compound | Amount (mg/tablet) |
| --- | --- |
| Org 31710 | 5 |
| corn starch | 6.500 |
| povidone | 1.950 |
| stearic acid | 0.650 |
| colloidal silicone dioxide | 0.650 |
| dl-α-tocopherol | 0.080 |
| lactose | qsad 65.000 |

The same coating layer as for tablet I was used.

The tablets were packed in push-through packs as follows:
1 Tablet II
13 Tablets I
1 Tablet III
13 Tablets I The push through packs are placed in folding cartons, which are additionally sealed in aluminum sachets.

EXAMPLE II

The tablets of Example I, along with similar tablets containing 0.030 and 0.050 mg of desogestrel were tested in healthy female volunteers in a non-public, double-blind randomized study. Ovulation was completely inhibited with the tablets of Example I. Furthermore, the use of the tablets of Example I also had a low percentage of bleeding and spotting days in comparison to conventional regimens of desogestrel.

We claim:

1. A contraceptive kit, comprising:
    a total of 20 to 32 sequential daily dosage units, divided into four to eight phases, containing a progestogen as the sole contraceptively effective ingredient and
    wherein two or more of said dosage units further contain an anti-progestogen,
    wherein said phases intermittently contain one of said anti-progestogen dosage units.

2. The contraceptive kit of claim 1, wherein said kit has four phases and comprises two anti-progestogen dosage units.

3. The contraceptive kit of claim 1, further comprising placebo dosage units.

4. The contraceptive kit of claim 2, further comprising placebo dosage units.

5. The contraceptive kit of claim 2, wherein the dosage of one anti-progestogen dosage unit is lower than the dosage of the other anti-progestogen dosage unit.

6. The contraceptive kit of claim 2, wherein the progestogen is desogestrel present in a quantity of 75 μg per dosage unit and the anti-progestogen is Org 31710 present in a quantity of 25 mg in one phase and in a quantity of 3.5 to 12.5 mg in another phase.

7. A HRT (hormone replacement therapy) kit, comprising:
    a total of 20 to 32 sequential daily dosage units, divided into four to eight phases, containing as the sole hormone replacement effective ingredient a progestogen with or without an estrogen, and
    wherein two or more of said dosage units further contain an anti-progestogen,
    wherein said phases intermittently contain one of said anti-progestogen dosage units.

8. The HRT kit of claim 7, wherein said kit has four phases and comprises two anti-progestogen dosage units.

9. The HRT kit of claim 7, further comprising placebo dosage units.

10. The HRT kit of claim 8, further comprising placebo dosage units.

11. The HRT kit of claim 8, wherein the dosage of one anti-progestogen dosage unit is lower than the dosage of the other anti-progestogen dosage unit.

12. The HRT kit of claim 8, wherein the progestogen is desogestrel present in a quantity of 75 μg per dosage unit and the anti-progestogen is org 31710 present in a quantity of 25 mg in one phase and in a quantity of 3.5 to 12.5 mg in another phase.

13. A contraceptive method, comprising:
    administering to a patient during a menstrual cycle daily dosage units containing a progestogen as the sole contraceptively effective ingredient; and
    administering two or more dosage units comprising an anti-progestogen, wherein said anti-progestogen dosage units are administered intermittently during the cycle.

14. The contraceptive kit of claim 13, wherein the anti-progestogen dosage units are administered intermittently every 4 to 15 days.

15. The contraceptive method of claim 14, wherein two anti-progestogen dosage units are administered.

16. An HRT (hormone replacement therapy) method, comprising:

administering to a patient during a menstrual cycle daily dosage units containing as the hormone replacement effective ingredient a progestogen with or without estrogen, and administering two or more dosage units comprising an anti-progestogen, wherein said anti-progestogen dosage units are administered intermittently during the cycle.

17. The HRT method of claim 16, wherein the anti-progestogen dosage units are administered intermittently every 4 to 15 days.

18. The HRT method of claim 17, wherein two anti-progestogen dosage units are administered.

* * * * *